(12) United States Patent
Leconte

(10) Patent No.: US 8,772,477 B2
(45) Date of Patent: Jul. 8, 2014

(54) PROCESS FOR PREPARING LACTAMS

(75) Inventor: Philippe Leconte, Ribeauvillé (FR)

(73) Assignee: Rhodia Operations, Aubervilliers (FR)

( * ) Notice: Subject to any disclaimer, the term of this patent is extended or adjusted under 35 U.S.C. 154(b) by 30 days.

(21) Appl. No.: 13/260,268

(22) PCT Filed: Apr. 27, 2010

(86) PCT No.: PCT/EP2010/055588
§ 371 (c)(1),
(2), (4) Date: Dec. 9, 2011

(87) PCT Pub. No.: WO2010/125040
PCT Pub. Date: Nov. 4, 2010

(65) Prior Publication Data
US 2012/0095212 A1    Apr. 19, 2012

(30) Foreign Application Priority Data
Apr. 27, 2009 (FR) ..................... 09 52744

(51) Int. Cl.
*C07D 201/18* (2006.01)
(52) U.S. Cl.
USPC ........................................................ 540/539
(58) Field of Classification Search
USPC ........................................................ 540/539
See application file for complete search history.

(56) References Cited

U.S. PATENT DOCUMENTS

| | | | |
|---|---|---|---|
| 2,357,484 A | 9/1944 | Martin et al. |
| 4,628,085 A | 12/1986 | Mares et al. |
| 5,493,021 A | 2/1996 | Barratt et al. |
| 5,981,790 A | 11/1999 | Cotting et al. |
| 6,069,246 A | 5/2000 | Chiarelli et al. |
| 6,100,396 A | 8/2000 | Gayet et al. |
| 6,262,259 B1 | 7/2001 | Cotting et al. |
| 6,384,283 B1 | 5/2002 | Leconte |
| 6,478,968 B1 | 11/2002 | Perrona et al. |
| 6,479,658 B1 | 11/2002 | Brunelle et al. |
| 6,521,779 B1 | 2/2003 | Boschat et al. |
| 6,559,333 B1 | 5/2003 | Brunelle et al. |
| 6,635,151 B1 | 10/2003 | Bocquenet et al. |
| 6,835,830 B1 | 12/2004 | Bocquenet et al. |
| 7,060,820 B1 | 6/2006 | Sengupta et al. |
| 2002/0030014 A1 | 3/2002 | Leconte |
| 2003/0155299 A1 | 8/2003 | Carvin et al. |
| 2004/0116691 A1 | 6/2004 | Rosier et al. |
| 2004/0204603 A1 | 10/2004 | Leconte et al. |
| 2004/0220423 A1 | 11/2004 | Leconte et al. |
| 2008/0319220 A1 | 12/2008 | Leconte |

FOREIGN PATENT DOCUMENTS

| | | |
|---|---|---|
| EP | 0659741 A1 | 6/1995 |
| WO | 9618603 A1 | 6/1996 |
| WO | 96/22974 A1 | 8/1996 |
| WO | 97/46306 A1 | 12/1997 |
| WO | 98/05636 A1 | 2/1998 |
| WO | 98/17641 A1 | 4/1998 |
| WO | 99/54285 A1 | 10/1999 |
| WO | 99/59962 A1 | 11/1999 |
| WO | 99/67214 A1 | 12/1999 |
| WO | 00/05203 A1 | 2/2000 |
| WO | 00/06540 A1 | 2/2000 |
| WO | 00/27806 A1 | 5/2000 |
| WO | 00/31031 A1 | 6/2000 |
| WO | 01/49665 A2 | 7/2001 |
| WO | 02/074739 A1 | 9/2002 |
| WO | 03/000650 A2 | 1/2003 |
| WO | 03/000651 A2 | 1/2003 |
| WO | 2007/045750 A1 | 4/2007 |

OTHER PUBLICATIONS

Written Opinion of the International Searching Authority (Form PCT/ISA/237) issued by WIPO in PCT/EP2010/055588 on Nov. 1, 2011, and an English language translation of the Written Opinion.

*Primary Examiner* — Bruck Kifle
(74) *Attorney, Agent, or Firm* — Dentons US LLP

(57) ABSTRACT

A method for preparing lactams by cyclizing hydrolysis of a corresponding aminonitrile is described. A method for manufacturing a lactam by reacting an aminonitrile with water in the presence of a catalyst involving placing the water and the aminonitrile in contact in vapor phase, passing the mixture of vapors through a bed of catalyst arranged in at least one tube forming a reaction chamber and recovering the lactam at the outlet of the tube is also described.

4 Claims, No Drawings

PROCESS FOR PREPARING LACTAMS

This application is the United States national phase of PCT/EP2010/055588, filed Apr. 27, 2010, and designating the United States (published in the French language on Nov. 4, 2010, as WO 2010/125040 A1; the title and abstract were also published in English) and claims priority under 35 U.S.C. §119 of FR 0952744, filed Apr. 27, 2009, each hereby expressly incorporated by reference in its entirety and each assigned to the assignee hereof.

The present invention relates to a process for preparing lactams by cyclizing hydrolysis of the corresponding aminonitrile.

Aliphatic lactams, in particular such as $\epsilon$-caprolactam are base compounds for the preparation of polymers such as polyamides. $\epsilon$-Caprolactam is the base monomer for the manufacture of polyamide PA-6, a polymer used in numerous applications such as, for example, the textile industry, the industry of moulded or injection-moulded parts for numerous fields such as the automotive industry, electrical connectors, electrical household appliances, etc.

Among the known processes for manufacturing a lactam, the process in question according to the invention consists in reacting an aminonitrile with water in the presence of a catalyst in order to carry out a cyclizing hydrolysis of the aminonitrile to lactam.

This process is described in numerous patents. Mention may be made, by way of example, of U.S. Pat. No. 2,357,484 which describes a process for the vapour-phase preparation of a lactam, which consists in passing a mixture of water and of aminonitrile over a catalyst, such as activated alumina, a silica gel or borophosphoric acid.

U.S. Pat. No. 4,628,085 also proposes a process for preparing lactams that consists in bringing into contact, in the vapour phase, an aliphatic or aromatic aminonitrile and water in the presence of a catalyst based on silica in spherical form that has a BET surface area greater than 350 $m^2/g$ and a pore diameter of less than 20 nm, generally in the presence of ammonia and hydrogen.

A process has also been proposed by patent EP 0 805 801 for manufacturing lactam via cyclizing hydrolysis of an aminonitrile in the presence of a catalyst, an activated alumina having particular porosity and specific surface area characteristics. This catalyst has a very long service life compared to other catalysts. Other features of this process have been described in patents EP 0 659 741, EP 0 805 801, EP 1 089 972, EP 1 098 875 and EP 1 370 524.

This reaction is generally carried out in a tubular reactor, the catalyst being positioned in each tube.

The cyclizing hydrolysis reaction is exothermic and therefore it is necessary to discharge the heat released in order to maintain a temperature which makes it possible, on the one hand, to have a sufficient reaction rate and, on the other hand, to minimize the formation of by-products.

One of the objectives of the present invention is to propose a process that makes it possible to control the temperature in the tubular reactor in order to have a high productivity while retaining a very high lactam selectivity.

For this purpose, the invention proposes a process for manufacturing lactam by reaction of an aminonitrile with water in the presence of a catalyst that consists in bringing into contact, in the vapour phase, water and aminonitrile, in passing the mixture of vapours through a catalyst bed positioned in at least one tube that forms a reactor and in recovering the lactam at the tube outlet.

According to the invention, the process comprises cooling means in order to make it possible to maintain the temperature, at any point of the tube, at a value below 340° C. and at a value above 280° C.

Indeed, in order to avoid the formation of by-products and therefore to increase the selectivity of the reaction to caprolactam, it is important to maintain the temperature in the reactor tube at a value below 340° C., especially in the first upstream part of the tube where the amount of heat released by the reaction is greatest.

Moreover, in order to obtain optimal productivity of the process, it is also necessary for the temperature in the reactor tube not to drop below 280° C. approximately.

According to the invention, this control of the temperature in the tube of the reactor and especially over the entire length of the tube is obtained by the use of at least two different cooling means:

A first means of cooling a first part of the reactor known as the "upstream part" having a sufficient heat discharging ability in order to prevent an increase of the temperature to a value above 340° C. approximately.

A second means of cooling the other part of the reactor tube known as the "downstream part" that makes it possible to maintain the temperature of the tube at a value above 280° C. approximately and below 340° C. approximately. The second cooling means has a heat discharging ability different from that of the first means. Indeed, the amount of heat released by the reaction between the water and the aminonitrile is lower in this part of the tube, considering that the water and aminonitrile concentrations have decreased. Therefore, the risk of having very high temperatures is reduced. However, it is necessary to maintain the temperature at a certain level in order to have a sufficient reaction rate and sufficient productivity.

In one preferred embodiment of the invention, the cooling means are constituted by devices that allow the circulation of a coolant such as oils and/or molten salts. The temperature of this coolant is different in the two cooling zones.

Advantageously, the temperature of the first cooling means is between 280° C. and 310° C. Preferably, the temperature of the second cooling means is between 290° C. and 340° C.

Moreover, without departing from the scope of the invention, it is possible to use a number of cooling zones that is greater than 2, each cooling means making it possible to control one part of the reactor tube, and the heat discharging ability of each means being adapted to the amount of heat released by the reaction in the part of the tube in question, by adjusting the temperature.

Generally, the reactor used is a tubular reactor comprising a large number of tubes positioned parallel. Each tube is filled with a solid catalyst, advantageously in powder or granule form. The upstream end of this reactor comprises means of feeding aminonitrile and water in vapour form.

The cooling means are generally constituted by the circulation of a liquid heat-transfer fluid that bathes the tubes of the reactor.

The cooling means may be uniquely constituted by an inlet of a heat-transfer fluid into the shell of the reactor and an outlet for said fluid. The tubes are thus immersed in the heat-transfer fluid.

Thus, in one embodiment of the invention, the tubular reactor comprises an upstream zone, in which a heat-transfer fluid circulates around the tubes, and a second downstream zone in which a heat-transfer fluid, generally at a temperature above that of the heat-transfer fluid circulating in the first zone, circulates. Each cooling zone may advantageously be separated by a seal plate.

The upstream part of the reactor or of the tube represents, according to one feature of the invention, from 0.1 to 0.3 times the length of the reactor or of the tube. Thus, for an industrial-scale reactor, the length of the upstream part is between 0.5 m and 1.5 m, the total length of the tube or reactor advantageously being between 3.5 m and 7 m.

The process for hydrolysis of an aminonitrile such as aminocapronitrile to caprolactam is carried out with a hydrolysis catalyst, especially an optionally doped activated alumina. Suitable catalysts for the invention are described, for example, in European Patents No. 0 805 801 and No. 1 098 875. Other solid hydrolysis catalysts may be used, such as those described in Patent EP 0 659 741.

The aminonitrile used in the process of the invention is more particularly a linear or branched aliphatic aminonitrile having from 3 to 12 carbon atoms.

As examples, mention may be made of the aminonitriles obtained by hydrogenation of a nitrile functional group of dinitrile compounds such as adiponitrile, methylglutaronitrile, ethylsuccinonitrile, dimethylsuccinonitrile, malononitrile, succinonitrile, glutaronitrile and dodecanedinitrile.

The most important aminonitrile is the aminocapronitrile obtained by partial hydrogenation of adiponitrile. The cyclizing hydrolysis of this compound results in ε-caprolactam, which is an important monomer for the manufacture of polyamides, especially polyamide PA-6.

The aminonitrile and the water are introduced into the tubes of the reactor in vapour form.

Advantageously, the aminonitrile is vaporized by contact with the water vapour and therefore the duration of contact between the water vapour and the aminonitrile in the absence of catalyst is minimized. This method of carrying out the introduction of the reactants is described in European Patent No. 1 089 972.

Other features of the process for the hydrolysis of aminonitrile to lactam are described in the literature such as, for example, in Patent EP 0 938 473. The lactam recovered is purified by distillation, in order, in particular, to separate the water and the light and heavy products.

Lactam purification processes are described in European Patents No. 0 922 027, 1 105 374, 1 131 287 and 1 242 375.

These purification processes comprise steps of acid treatment over ion-exchange resin and also dehydration columns in order to remove water from the lactam. The water thus recovered in the dehydration column may advantageously be used as a reactant in the cyclizing hydrolysis step. The vaporization of this aqueous stream may advantageously be obtained by heat exchange with the vapours exiting the hydrolysis reactor in order to obtain a pre-condensation of these vapours.

The aminonitrile used in the process of the invention may be obtained by any known process. However, in one preferred embodiment of the invention, especially when the lactam is ε-caprolactam, the aminonitrile is the aminocapronitrile obtained by hemihydrogenation of adiponitrile. These hemihydrogenation processes are described in numerous patents, such as EP 1 397 346, EP 1 397 345, EP 0 797 568, EP 0 925 106 and EP 1 127 047.

The hemihydrogenation products comprising the solvent, the diamine, the aminonitrile and the non-hydrogenated dinitrile are separated by successive distillations. Processes for separating products resulting from the hemihydrogenation are described in the literature, and especially European Patents No. 1 071 657, No. 1 077 932 and Patent WO 2007/045750.

In the case where the solvent of the hemihydrogenation reaction is water, this, after separation by distillation, may advantageously be used in another step of the process for preparing caprolactam such as, for example, in the step of pre-washing before regeneration of the ion-exchange resins used in the purification of the caprolactam.

In the case of the hemihydrogenation of adiponitrile, the hexamethylenediamine is separated from the aminocapronitrile by distillation in a distilling column (A) as the overhead fraction of the column. This crude hexamethylenediamine may advantageously undergo another distillation in a distilling column (B). The pure hexamethylenediamine is then drawn off as pasteurized on one of the plates of the column (B) whereas, at the top of the column, the compounds known as light compounds are removed, and the bottom fraction or residue is recycled as reflux into the distilling column (A).

Other details and advantages of the invention will appear in light of the examples given below solely by way of indication and illustration. The examples below are carried out in a vertical multitubular reactor having 55 tubes of 4 m in length. Each tube is filled with an activated alumina used as catalyst and having the following characteristics:

Specific surface are a (SSA): 139 $m^2/g$
Total pore volume: 117 ml/100 g
Pore volume corresponding to the pores with a diameter greater than 500 Å: 50 ml/100 g
Pore volume corresponding to the pores with a diameter greater than 200 Å: 70 ml/100 g
Pore volume corresponding to the pores with a diameter greater than 70 Å: 116 ml/100 g.

Two of the filled tubes also contain a temperature probe in order to monitor the temperature profile. In order to guarantee a good homogeneity of the heat exchange over each of the tubes, chicanes and recirculating pumps are positioned, in an optimized manner, as a function of the general knowledge in the heat exchange field. Thus, the maximum temperature difference of the heat-transfer fluid between its inlet into the shell of the reactor and its outlet is 2° C.

COMPARATIVE EXAMPLE 1

The reactor has only a single cooling zone or a single cooling means. The heat-transfer fluid enters at the bottom of the shell of the reactor and emerges at the top.

A vapour stream composed of 38 kg/h of aminocapronitrile (ACN) and of 24.5 kg/h of water continuously feeds the top of the hydrolysis reactor.

The inlet temperature of the heat-transfer fluid is set in order to maintain the temperature at the hottest spot of the catalyst at most at 340° C.±1° C. This hot point lies between 0.2 and 0.3 m below the inlet of the reactor tubes containing the catalyst.

The table below gives the inlet temperature of the heat-transfer fluid, the conversion of the ACN and the caprolactam (CL) selectivity as a function of the time.

| Time in hours | 24 | 300 | 500 |
|---|---|---|---|
| Heat-transfer fluid temperature ° C. | 282 | 286 | 289 |
| ACN conversion % | 99.4 | 99.2 | 99.1 |
| CL selectivity % | ≥99.8 | ≥99.8 | ≥99.8 |

In order to compensate for the deactivation of the catalyst and to maintain the hot spot at 340° C., the temperature of the heat-transfer fluid must be gradually increased.

Despite the increase in temperature, the caprolactam selectivity is not adversely affected but the ACN conversion gradually decreases.

EXAMPLE 2

Example 1 is repeated in a similar manner but with the difference that the reactor has two distinct cooling zones separated by a plate. The temperatures of these zones are regulated independently. The first zone has a length of 1 m and is used for limiting the hot spot at the inlet of the reactor to at most 340° C.

The second zone of 3 m allows the highest possible conversion rate of the ACN.

The table below gives the inlet temperatures of the heat-transfer fluid in the two zones, the conversion of the ACN and the caprolactam (CL) selectivity as a function of the time.

| Time in hours | 24 | 300 | 500 |
|---|---|---|---|
| Heat-transfer fluid temperature ° C. Zone 1 (upstream) | 282 | 286 | 289 |
| Heat-transfer fluid temperature ° C. Zone 2 (downstream) | 300 | 300 | 300 |
| ACN conversion % | 99.5 | 99.5 | 99.5 |
| CL selectivity % | ≥99.8 | ≥99.8 | ≥99.8 |

After 500 hours of continuous operation it is observed that the conversion of the ACN is maintained by setting the temperature of the second zone at 300° C.

The invention claimed is:

1. A process for manufacturing a lactam from a linear or branched aliphatic aminonitrile having from 3 to 12 carbon atoms, the process comprising reacting said aminonitrile with water by forming a mixture of vapors of said aminonitrile and water by bringing into contact, in a vapor phase, water and said aminonitrile, passing said mixture of vapors through a catalyst bed positioned in at least one tube that forms a reactor and recovering the lactam at a tube outlet, wherein the aminonitrile is aminocapronitrile and the lactam is ε-caprolactam, and wherein the temperature in the tube is controlled by cooling means to maintain the temperature throughout the length of the tube at a value between 280° C. and 340° C., said cooling means comprising at least two distinct means, a first cooling means which controls the temperature in an upstream part of the tube in order to maintain the temperature at a value below 340° C., and a second cooling means positioned around a downstream part of the tube in order to maintain the temperature of the tube at a value above 280° C. and below 340° C.

2. The process according to claim 1, wherein the temperature of the means intended to control the temperature in the upstream part of the tube is between 280° C. and 310° C.

3. The process according to claim 1, wherein the temperature of the means positioned around the downstream part of the tube is between 290° C. and 340° C.

4. The process according to claim 1, wherein the upstream part of the tube has a length between 0.5 m and 1.5 m, the total length of the tube being between 3.5 m and 7 m.

* * * * *